US012558113B2

(12) United States Patent
Crawford et al.

(10) Patent No.: US 12,558,113 B2
(45) Date of Patent: Feb. 24, 2026

(54) MEDICAL EXTRACTION ASSEMBLIES AND METHODS OF USING THE SAME

(71) Applicant: Boston Scientific Scimed Inc., Maple Grove, MN (US)

(72) Inventors: Richard Crawford, Galway (IE); Enda Connaughton, Galway (IE)

(73) Assignee: Boston Scientific Scimed Inc., Maple Grove, MN (US)

( * ) Notice: Subject to any disclaimer, the term of this patent is extended or adjusted under 35 U.S.C. 154(b) by 421 days.

(21) Appl. No.: 17/458,055

(22) Filed: Aug. 26, 2021

(65) Prior Publication Data

US 2022/0061866 A1     Mar. 3, 2022

Related U.S. Application Data

(60) Provisional application No. 63/071,253, filed on Aug. 27, 2020.

(51) Int. Cl.
*A61B 17/221*     (2006.01)
*A61B 17/00*     (2006.01)
*A61B 17/22*     (2006.01)

(52) U.S. Cl.
CPC .. *A61B 17/221* (2013.01); *A61B 2017/00818* (2013.01); *A61B 2017/22067* (2013.01); *A61B 2017/2215* (2013.01)

(58) Field of Classification Search
CPC .......... A61B 17/221; A61B 2017/2215; A61B 17/22; A61B 17/22031–22032
See application file for complete search history.

(56) References Cited

U.S. PATENT DOCUMENTS

| | | | | |
|---|---|---|---|---|
| 4,024,873 | A | * | 5/1977 | Antoshkiw ............ A61B 5/028 |
| | | | | 604/917 |
| 4,627,837 | A | | 12/1986 | Gonzalo |
| 5,102,415 | A | * | 4/1992 | Guenther ............... A61B 17/22 |
| | | | | 604/103.05 |

(Continued)

FOREIGN PATENT DOCUMENTS

| | | |
|---|---|---|
| EP | 2283892 A2 | 2/2011 |
| JP | 2001149377 A | 6/2001 |

OTHER PUBLICATIONS

International Search Report and Written Opinion issued on Dec. 3, 2021, in counterpart International Patent Application No. PCT/US2021/071294 (20 pages, in English).

*Primary Examiner* — Elizabeth Houston
*Assistant Examiner* — Jonathan A Hollm
(74) *Attorney, Agent, or Firm* — Bookoff McAndrews PLLC

(57) ABSTRACT

A medical device that includes an outer shaft, an inner shaft disposed within the outer shaft, and a tube disposed within the inner shaft and the outer shaft. The medical device includes a first expandable member having a proximal end secured to the outer shaft and a distal end secured to the inner shaft. The inner shaft and the tube are received through the first expandable member. The first expandable member is configured such that the proximal end is movable relative to the distal end when the outer shaft moves relative to the inner shaft. The first expandable member is configured to radially expand when the proximal end moves toward the distal end and radially compress when the proximal end moves away from the distal end.

9 Claims, 6 Drawing Sheets

(56)　　　　　References Cited

U.S. PATENT DOCUMENTS

| | | | | |
|---|---|---|---|---|
| 5,449,372 | A * | 9/1995 | Schmaltz | A61F 2/88 |
| | | | | 606/198 |
| 6,383,205 | B1 * | 5/2002 | Samson | A61F 2/013 |
| | | | | 606/200 |
| 6,626,861 | B1 * | 9/2003 | Hart | A61M 25/10 |
| | | | | 604/96.01 |
| 6,692,484 | B1 * | 2/2004 | Karpiel | A61B 17/22031 |
| | | | | 606/191 |
| 9,642,637 | B1 | 5/2017 | Lind et al. | |
| 9,743,944 | B1 * | 8/2017 | Bonneau | A61B 17/225 |
| 10,004,531 | B2 * | 6/2018 | Rosenbluth | A61B 17/221 |
| 10,478,204 | B2 | 11/2019 | Bonneau et al. | |
| 11,376,027 | B2 * | 7/2022 | Martin | A61B 17/221 |
| 2004/0260333 | A1 * | 12/2004 | Dubrul | A61M 29/02 |
| | | | | 606/200 |
| 2010/0298634 | A1 | 11/2010 | Yanuma | |
| 2013/0030460 | A1 * | 1/2013 | Marks | A61B 17/221 |
| | | | | 606/200 |
| 2013/0165944 | A1 | 6/2013 | Gal et al. | |
| 2017/0020556 | A1 * | 1/2017 | Sutton | A61B 17/12109 |
| 2019/0380722 | A1 * | 12/2019 | Lorenzo | A61B 17/221 |

* cited by examiner

MEDICAL EXTRACTION ASSEMBLIES AND METHODS OF USING THE SAME

CROSS-REFERENCE TO RELATED APPLICATIONS

This application claims the benefit of priority from U.S. Provisional Application No. 63/071,253, filed on Aug. 27, 2020, which is incorporated by reference herein in its entirety.

TECHNICAL FIELD

Various aspects of the disclosure relate generally to medical extraction systems, devices, and related methods. Examples of the disclosure relate to systems, devices, and related methods for providing a medical instrument with multiple expandable elements, among other aspects.

BACKGROUND

Technological developments have given users of medical systems, devices, and methods, the ability to conduct increasingly complex procedures on subjects. One challenge in the field of minimally invasive surgeries is associated with extracting objects from within a subject, such as a biliary stone from the bile duct of patient. Such procedures may require the use of multiple instruments for performing removal of the biliary stone, including a device to trawl the bile duct, a device to dilate an ampulla, and a device to extract the biliary stone. Requiring use of multiple instruments during the procedure may cause various procedural issues and/or increase risk of injury to the subject.

SUMMARY

Aspects of the disclosure relate to, among other things, systems, devices, and methods for providing a medical device capable of extracting an object from within a subject, among other aspects. Each of the aspects disclosed herein may include one or more of the features described in connection with any of the other disclosed aspects.

According to an example, a medical device includes an outer shaft, an inner shaft disposed within the outer shaft, and a tube disposed within the inner shaft and the outer shaft. The medical device includes a first expandable member having a proximal end secured to the outer shaft and a distal end secured to the inner shaft. The inner shaft and the tube are received through the first expandable member. The first expandable member is configured such that the proximal end is movable relative to the distal end when the outer shaft moves relative to the inner shaft. The first expandable member is configured to radially expand when the proximal end moves toward the distal end and radially compress when the proximal end moves away from the distal end.

Any of the medical devices described herein may include one or more of the following features. The outer shaft and the inner shaft are configured to increase a width and decrease a length of the first expandable member when the inner shaft moves proximally relative to the outer shaft. The first expandable member is configured to decrease the width and increase the length of the first expandable member when the inner shaft moves distally relative to the outer shaft. The first expandable member includes a stent having a flexible body. The medical device includes a second expandable member disposed about the tube such that the tube extends through the second expandable member. The second expandable member is in fluid communication with a lumen of the tube and configured to receive a fluid from the lumen. The second expandable member is configured to move relative to the tube in response to receiving the fluid from the lumen. The second expandable member includes an inflatable balloon. The medical device includes a third expandable member secured to the inner shaft and positioned distally to the distal end of the first expandable member. The third expandable member is disposed about the tube such that the tube extends through the third expandable member. The third expandable member is configured to move from a compressed state to an expanded state in response to the third expandable member extending outwardly from an outer tube. The proximal end of the third expandable member has a same configuration in the compressed state and the expanded state of the third expandable member. A distal portion of the third expandable member expands radially outward when transitioning from the compressed state to the expanded state of the third expandable member. The third expandable member includes a plurality of wires distal of the distal end of the first expandable member. The plurality of wires define a cavity configured to engage an object received within the cavity. The third expandable member is configured to inhibit release of the object received within the cavity of the plurality of wires. The third expandable member is configured to engage the second expandable member in response to the tube moving relative to the inner shaft.

According to another example, a medical device includes a first shaft, a second shaft disposed within and configured to move relative to the first shaft, and a third shaft disposed within and configured to move relative to the second shaft. The medical device includes a first expandable member having a proximal end secured to the first shaft and a distal end secured to the second shaft. The distal end is configured to move relative to the proximal end in response to the second shaft moving relative to the first shaft. The first shaft and the second shaft are configured to increase a width and decrease a length of the first expandable member when the distal end moves toward the proximal end, and to decrease the width and increase the length of the first expandable member when the distal end moves away from the proximal end. The medical device includes a second expandable member disposed about the third shaft such that the third shaft extends through the second expandable member. The second expandable member is in fluid communication with a lumen of the third shaft and configured to expand radially outward in response to receiving a fluid from the lumen.

Any of the medical devices described herein may include one or more of the following features. The medial device includes a third expandable member secured to the second shaft and positioned distally to the first expandable member. The third expandable member is disposed about the third shaft such that the third shaft extends through the third expandable member. The third expandable member defines a cavity having a distally-facing opening configured to receive an object. The second expandable member is configured to engage the object received within the cavity in response to the third shaft moving proximally relative to the inner shaft.

According to a further example, a method of retrieving an object from a body, including positioning a first expandable member in the body and proximal of the object and positioning a second expandable member in the body and distal of the object such that the object is bounded by the first expandable member and the second expandable member. The method includes expanding the first expandable member and the second expandable member to expand a lumen in the body. The object is positioned in the lumen. The method includes moving the first expandable member and the second expandable member proximally relative to the lumen to remove the object from the body.

Any of the methods described herein may include one or more of the following steps. Prior to moving the first expandable member and the second expandable member relative to the lumen, the method further includes expanding a third expandable member positioned between the first expandable member and the second expandable member. The third expandable member defines a cavity. The method further includes receiving the object within the cavity of the third expandable member.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Examples of the disclosure include systems, devices, and methods for providing a medical instrument including an extraction assembly having expandable members that are selectively expandable for collecting and removing a target object from a target treatment site within a patient.

As used herein, the term "distal" refers to a portion farthest away from a user when introducing a device into a patient and the term "proximal" refers to a portion closest to the user when placing the device into the subject. The terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). Various examples described herein include single-use or disposable medical devices, although some embodiments may include one or more reusable components of the device. Reference will now be made in detail to examples of the disclosure described above and illustrated in the accompanying drawings. Wherever possible, the same reference numbers will be used throughout the drawings to refer to the same or like parts.

Figure 1:
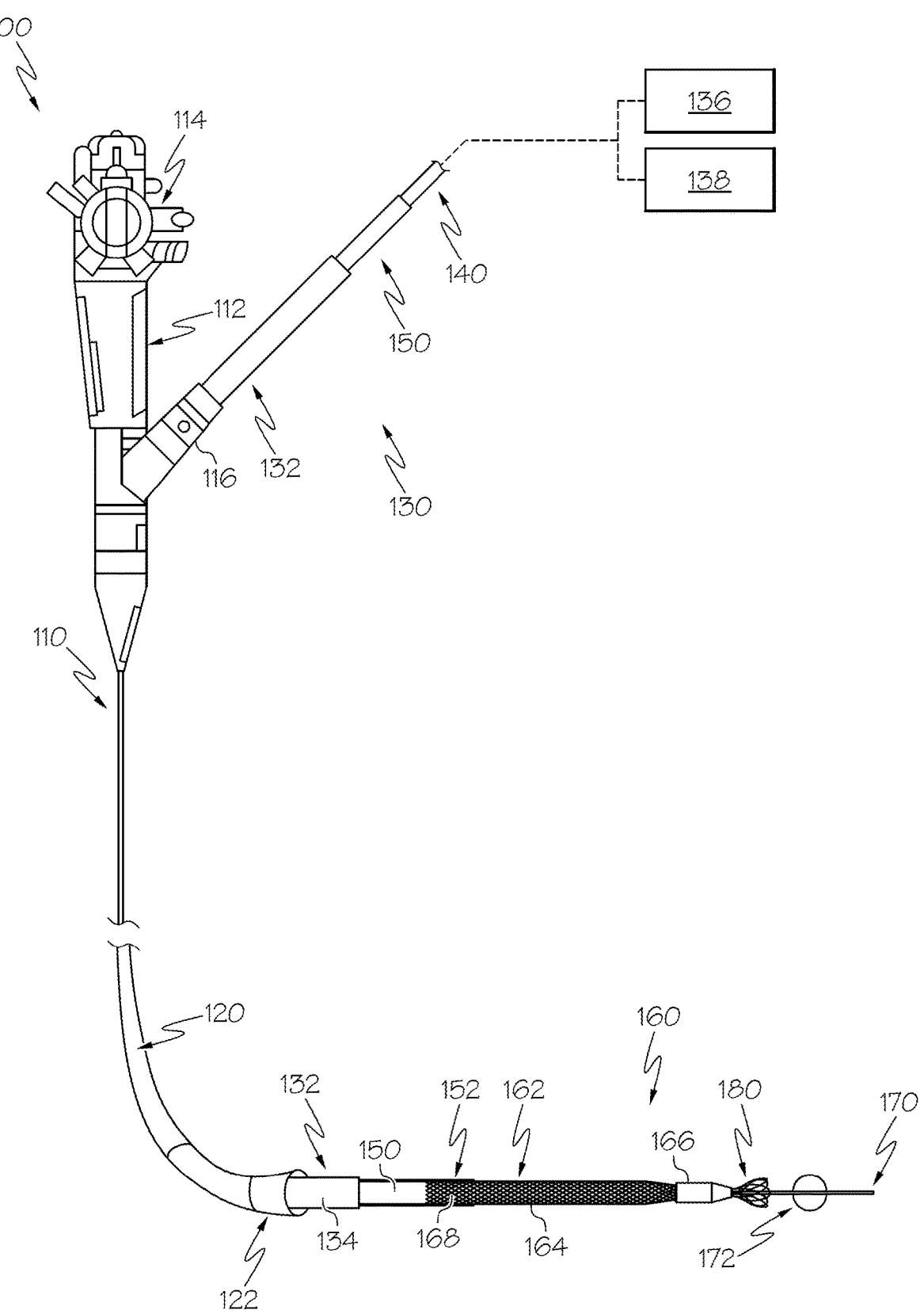
FIG. 1 is a perspective view of an exemplary medical instrument including an extraction assembly, according to aspects of this disclosure.

FIG. 1 shows an exemplary medical system 100 in accordance with an example of this disclosure. Medical system 100 may include a medical instrument 110 and a medical device 130. For example, medical instrument 110 may include an endoscope, duodenoscope, gastroscope, colonoscope, ureteroscope, bronchoscope, and/or various other delivery systems. Medical instrument 110 may include a handle 112, at least one actuator 114, one or more ports 116, and a shaft 120. Handle 112 may be defined by a proximal end including actuator 114 and a distal end including shaft 120 extending distally therefrom. The one or more ports 116 may extend outwardly from handle 112 and be configured to facilitate receipt of one or more devices into medical instrument 110. It should be appreciated that medical instrument 110 may include additional ports 116 than those shown and described herein.

Handle 112 may have one or more lumens (not shown) that communicate with a lumen(s) of one or more other components of medical instrument 110. The one or more ports 116 may open into the one or more lumens of handle 112. Ports 116 may be sized and shaped to receive one or more devices therethrough, such as, for example, medical device 130. Shaft 120 may include a tube that is sufficiently flexible such that shaft 120 is configured to selectively bend, rotate, and/or twist when being inserted into and/or through a subject's tortuous anatomy to a target treatment site (see FIG. 4). Shaft 120 may include a longitudinal length extending from a proximal end at handle 112 and a distal end 122.

It should be understood that shaft 120 may have one or more lumens extending therethrough that include, for example, a working lumen 121 (see FIG. 2) for receiving instruments, such as medical device 130. By way of further example, shaft 120 may include a fluid lumen for delivering a fluid, such as, for example, from a pressurized medium source (not shown) fluidly coupled to medical instrument 110. Shaft 120 may further include an additional fluid lumen for conveying fluid away from the distal end of medical instrument 110, such as during use of medical instrument 110 in a procedure. In other examples, shaft 120 may include additional lumens such as a control wire lumen for receiving one or more control wires for actuating one or more distal parts/tools (e.g., an articulation joint, an elevator, etc.), an illumination lumen for receiving at least a portion of an illumination assembly (e.g., optical fiber), and/or an imaging lumen for receiving at least a portion of an imaging assembly (e.g., camera, sensor, etc.). Distal end 122 may include one or more openings that are in communication with the one or more lumens of shaft 120.

Figure 2:
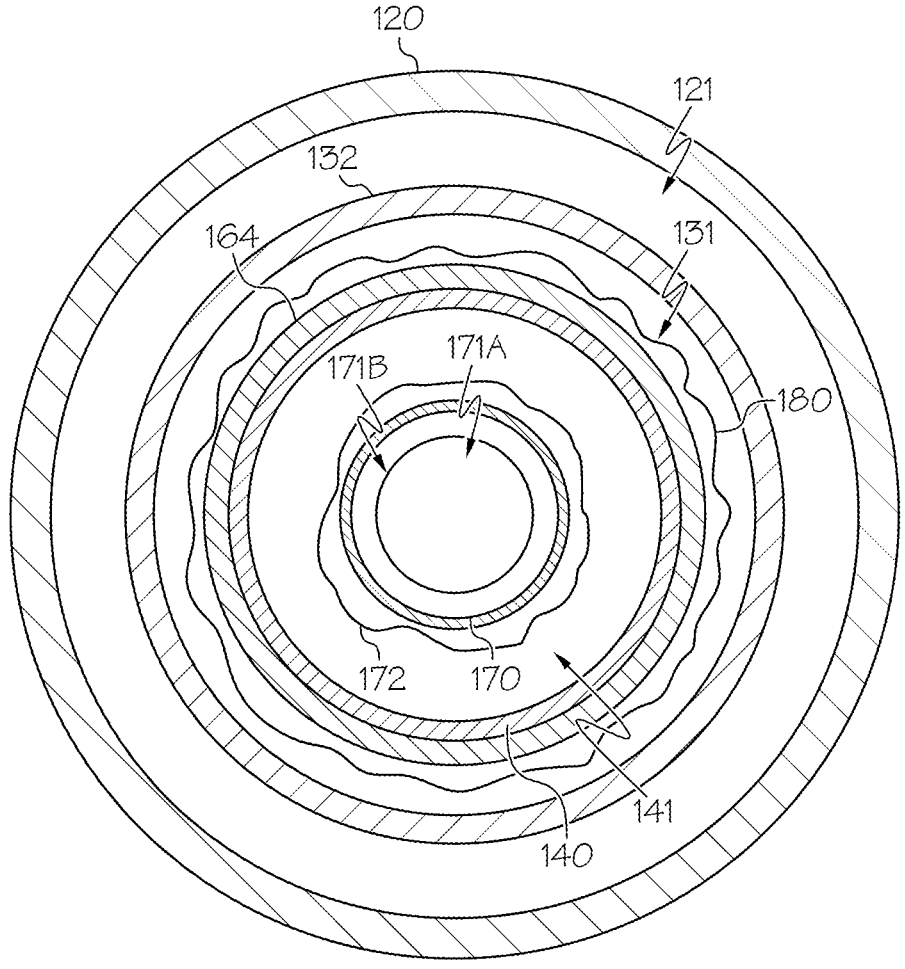
FIG. 2 is an end view of the extraction assembly of FIG. 1, also showing some components in cross-section when in an insertion configuration.

Still referring to FIG. 1, medical device 130 may include an outer tube 132, an inner shaft 140, an outer shaft 150, and an inner tube 170. Outer tube 132 may be received through port 116 and extend through shaft 120, with a proximal end of outer tube 132 extending proximally from handle 112 and a distal end 134 of outer tube 132 extending distally through an opening at distal end 122. As seen in FIG. 2, outer tube 132 may be received within working lumen 121 of shaft 120. Further, inner shaft 140, outer shaft 150, and inner tube 170 may be received through a lumen 131 of outer tube 132, and particularly inner shaft 140 and inner tube 170 may be received through a lumen of outer shaft 150. Accordingly, outer tube 132 may include a cross-sectional dimension that is greater than each of inner shaft 140, outer shaft 150, and inner tube 170. Further, outer shaft 150 may include a cross-sectional dimension that is greater than each of inner shaft 140 and inner tube 170. Inner tube 170 may be received through a lumen 141 of inner shaft 140 such that inner shaft 140 may include a cross-sectional dimension that is greater than inner tube 170. In some embodiments, inner shaft 140 may include a greater rigidity than inner tube 170.

FIG. 2 shows a combination of an end view and a cross-sectional view of medical system 100, and specifically of a distal end of medical device 130 extending outwardly from a distal end of medical instrument 110. As seen in FIG. 2, inner tube 170 may include one or more lumens 171A, 171B extending from a proximal end of inner tube 170 to a distal end of inner tube 170. In the example, lumens 171A, 171B may be separated from one another. For example, a first lumen 171A may be sized and shaped to receive one or more instruments, such as, for example, a guidewire, an imaging device, an illumination assembly, etc. First lumen 171A may extend from the proximal end of inner tube 170 to an opening at the distal end of inner tube 170, such that the instrument received therein may extend outwardly from the distal end of inner tube 170. A second lumen 171B may extend from the proximal end of inner tube 170 to second expandable member 172, such that second lumen 171B terminates proximal to the opening at the distal end of inner tube 170. As described in further detail herein, second lumen 171B may be configured to deliver a material, such as a gas or a liquid, to second expandable member 172.

Referring back to FIG. 1, medical device 130 may include one or more actuators at a proximal end of medical device 130, such as, for example, a first actuator 136 and a second actuator 138. As described in greater detail herein, first actuator 136 and second actuator 138 may be configured to move one or more of outer tube 132, inner shaft 140, outer shaft 150, and inner tube 170 relative to one another and/or to medical instrument 110. First actuator 136 and second actuator 138 may be further configured to actuate an extraction assembly 160 of medical device 130. It should be appreciated that medical device 130 may include additional and/or fewer actuators than those shown and described herein without departing from a scope of this disclosure.

Such actuators can be any mechanisms well known to those of skill in the art, to translate, expand, inflate, or perform any other movement or function of the various parts, including the structures at the distal end of medical device 130.

Medical device 130 may include extraction assembly 160 at a distal end of inner shaft 140, outer shaft 150, and inner tube 170. Extraction assembly 160 may include a first expandable member 162 having a body 164 defined by a distal end 166 and a proximal end 168. Proximal end 168 may be attached to a distal end 152 of outer shaft 150y, and distal end 166 may be attached to a distal end of inner shaft 140. In some embodiments, distal end 166 may include a sheath, a tube, a shaft, a coil, a wire, a string, and/or other device secured to a distal portion of body 164. Ends 166, 168 may be attached by various suitable methods, including, for example, an adhesive, molding, bonding, mechanical fixation, etc. With first expandable member 162 secured about distal end 152, it should be appreciated that inner shaft 140 and inner tube 170 may be received through a lumen of body 164 (see FIG. 2) when extending distally from outer shaft 150.

In some embodiments, first expandable member 162 may include a dilation stent configured to be selectively expanded and/or compressed in response to actuating one or more of actuators 136, 138. Actuators 136, 138 may include one or more markings (e.g., numbers, colors, lines, etc.) indicative of a corresponding dilation diameter of first expandable member 162 to facilitate a controlled expansion and/or compression of body 164. In further embodiments, a proximal portion of body 164, such as a portion adjacent to proximal end 168, may have a tapered profile to further provide controlled dilation of first expandable member 162. Body 164 may be formed of a flexible material and configured to provide frictional resistance between first expandable member 162 and an ancillary surface (e.g., a tissue wall) when contacting the ancillary surface.

Still referring to FIG. 1, extraction assembly 160 may further include a second expandable member 172 positioned adjacent to a distal end of inner tube 170. Second expandable member 172 may be disposed about an outer circumference of inner tube 170, proximal to the distal end of the inner tube 170. Second expandable member 172 may be formed of a flexible and/or elastic material that is movable relative to inner tube 170. Second expandable member 172 may be in fluid communication with second lumen 171B (see FIG. 2) and may include a dilation balloon configured to selectively inflate and/or deflate in response to receiving a material from second lumen 171B. For example, the material may include a pressurized fluid, such as gas (e.g., air, $CO_2$, etc.), liquid (e.g., saline, etc.), etc. As seen in FIG. 2, second expandable member 172 may have a cross-sectional profile that is smaller than lumen 141 of inner shaft 140 when second expandable member 172 is in a deflated state. Although not shown in FIG. 2, second expandable member 172 may have a greater cross-sectional profile than inner shaft 140 when in an inflated state. Second expandable member 172 may include various suitable sizes, shapes, and/or configurations when in the inflated state. For example, a body of second expandable member 172 may form a spherical, ovular, circular, cylindrical, torus (e.g., donut-shaped), and/or other various shapes.

Extraction assembly 160 may further include a third expandable member 180 positioned distally of first expandable member 162. In some embodiments, third expandable member 180 may be secured to distal end 166 of body 164. For example, a proximal end of third expandable member 180 may be received under, and attached to, distal end 166 by various suitable mechanisms (e.g., by crimping third expandable member 180 to distal end 166). In other embodiments, third expandable member 180 may be secured to the distal end of inner shaft 140. In some embodiments, third expandable member 180 may be configured to be selectively compressed and/or expanded in response to actuating one or more of actuators 136, 138. As described in further detail herein, third expandable member 180 may include a greater cross-sectional dimension relative to inner tube 140 and inner tube 170 when transitioned to an expanded state (see FIG. 2). As seen in FIG. 2, third expandable member 180 may have a cross-sectional profile that is greater than body 164 of first expandable member 162 when third expandable member 180 is in an expanded state. It should be understood that body 164 is positioned proximal of third expandable member 180 when third expandable member 180 is in the compressed state and the expanded state.

Figures 3A, 3B:
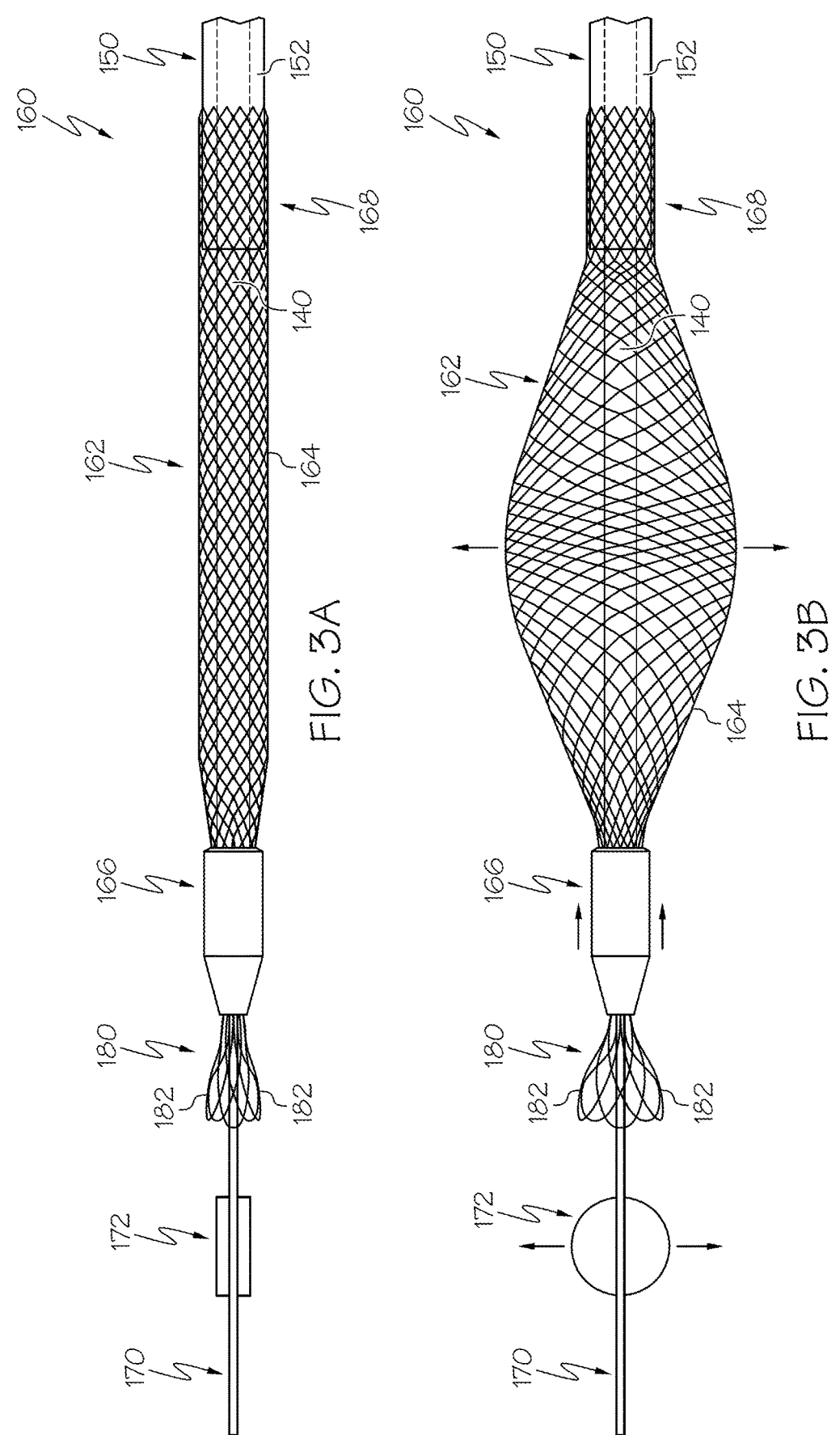
FIG. 3A is a partial side view of the medical instrument of FIG. 1 with the extraction assembly including three expandable members in contracted states, according to aspects of this disclosure.
FIG. 3B is a partial side view of the medical instrument of FIG. 1 with the three expandable members in expanded states, according to aspects of this disclosure.

Referring now to FIG. 3A, third expandable member 180 may include one or more wires 182 extending distally from first expandable member 162. The one or more wires 182 may define a cavity positioned distal to body 164. For example, third expandable member 180 may include a plurality of wires 182 that are interwoven with one another to collectively define the cavity. The plurality of wires 182 may flare (extend) radially outward relative to distal end 166, defining a distally-facing opening of third expandable member 180. The cavity formed by the plurality of wires 182 may include various sizes and/or shapes. The plurality of wires 182 may be formed of a flexible material, including, for example, a shape memory material (e.g., Nitinol), aluminum, plastic, metal, and various other elastic materials. Accordingly, the plurality of wires 182 may be manually manipulated to change a size and/or shape of the cavity and the distally-facing opening. In some embodiments, third expandable member 180 may include a cover connected to the plurality of wires 182 and disposed over the cavity. The cover may include a membrane that is positioned inside, on top, and/or embedded in the plurality of wires 182. The cover may inhibit an object (e.g., a stone) received in the cavity from moving proximally past third expandable member 180.

In the example shown in FIG. 3A, first expandable member 162 is depicted in a collapsed state such that body 164 includes a cross-sectional profile that is substantially similar to a cross-sectional profile of outer shaft 150. Further, a longitudinal length of body 164 (e.g., defined between distal end 166 and proximal end 168) may be relatively greater than the longitudinal length of body 164 when first expandable member 162 is in an expanded state (see FIG. 3B). With proximal end 168 attached to distal end 152, proximal end 168 is immovable relative to outer shaft 150 and translates longitudinally relative to inner shaft 140. Further, with distal end 166 attached to inner shaft 140, distal end 166 translates longitudinally relative to outer shaft 150 and is immovable relative to inner shaft 140.

Still referring to FIG. 3A, second expandable member 172 is depicted in a deflated state such that second expandable member 172 includes a cross-sectional profile that is relatively smaller than a cross-sectional profile of body 164, and specifically distal end 166. In this instance, inner tube 170 may move (e.g., translate) relative to body 164, such as extending distally from distal end 166 and/or retracting proximally through distal end 166, when in the deflated state. Further, with second expandable member 172 in the deflated state, second expandable member 172 includes a cross-sectional profile that is smaller than a cross-sectional profile of third expandable member 180. Accordingly, inner tube 170 may move (e.g., translate) relative to third expandable member 180, such as extending distally from and/or retracting proximally through third expandable member 180, when in the deflated state.

In FIG. 3A, third expandable member 180 is depicted in a compressed state such that third expandable member 180 includes a cross-sectional profile that is relatively smaller than a cross-sectional profile of third expandable member 180 when in an expanded state (see FIG. 3B). The plurality of wires 182 may be configured to flex radially inward to the compressed state in response to an application of force thereto. As described in further detail herein, an interior surface of outer tube 132 may be configured to apply a force against the plurality of wires 182 when third expandable member 180 is disposed within lumen 131 (see FIG. 2). In some embodiments, extraction assembly 160 may omit third expandable member 180 entirely.

Referring now to FIG. 3B, first expandable member 162 is depicted in an expanded state such that body 164 includes a cross-sectional profile that is substantially greater than a cross-sectional profile of outer shaft 150. First expandable member 162 may be configured to transition from the collapsed state (FIG. 3A) to the expanded state in response to inner shaft 140 and outer shaft 150 moving relative to one another. For example, body 164 may expand radially outward relative to inner shaft 140 and outer shaft 150 when distal end 166 translates proximally toward proximal end 168, or when proximal end 168 translates distally toward distal end 166. Additionally, body 164 may expand in response to both distal end 166 and proximal end 168 translating simultaneously toward one another.

In some embodiments, distal end 166 and/or proximal end 168 may be configured to expand and/or collapse with body 164, while in other embodiments one or more of distal end 166 and/or proximal end 168 may be configured to maintain a constant cross-sectional profile during movement of inner shaft 140 and/or outer shaft 150. In this instance, only an intermediate portion of body 164 may be selectively movable between the collapsed state and the expanded state. In some embodiments, at least a proximal portion of body 164 (e.g., adjacent to proximal end 168) may have a tapered profile relative to a remaining portion of body 164.

Still referring to FIG. 3B, second expandable member 172 is depicted in an inflated state such that second expandable member 172 includes a cross-sectional profile that is relatively greater than the cross-sectional profile of body 164 at distal end 166. In this instance, inner tube 170 may be at least partially inhibited from moving (e.g., translating) relative to body 164, such as retracting proximally through distal end 166, when second expandable member 172 is in the inflated state. Further, with second expandable member 172 in the inflated state, second expandable member 172 includes a cross-sectional profile that is greater than a cross-sectional profile at least a proximal portion of third expandable member 180. Accordingly, movement (e.g., translation) of inner tube 170 relative to third expandable member 180 may be inhibited, such as retracting proximally through third expandable member 180, when second expandable member 172 is in the inflated state.

In the inflated state, second expandable member 172 may be configured to engage third expandable member 180 when inner tube 170 is moved proximally relative to body 164. In this instance, second expandable member 172 may abut against a distal end of the plurality of wires 182, thereby limiting further movement of inner tube 170 proximally towards inner shaft 140 and/or outer shaft 150. As described in further detail herein, second expandable member 172 may be configured to move a target object toward third expandable member 180 and for receipt of the target object in the cavity between the plurality of wires 182 when second expandable member 172 is in the inflated state and third expandable member 180 is expanded. In embodiments in which third expandable member 180 may be omitted from extraction assembly 160, it should be understood that second expandable member 172 may be configured to engage distal end 166 when second expandable member 172 is in the inflated state and inner tube 170 is moved proximally relative to body 164.

Still referring to FIG. 3B, third expandable member 180 is depicted in an expanded state such that third expandable member 180 includes a cross-sectional profile that is relatively greater than the cross-sectional profile of third expandable member 180 when in the compressed state (see FIG. 3A). The plurality of wires 182 may be configured to flex radially outward in response to removing a force applied thereto. For example, a distal end of third expandable member 180 may expand while a proximal end of third expandable member 180 remains fixed. As described in further detail herein, a force applied against the plurality of wires 182 by the interior surface of outer tube 132 may be removed when third expandable member 180 extends outwardly from within lumen 131 (see FIG. 2).

Figure 4:
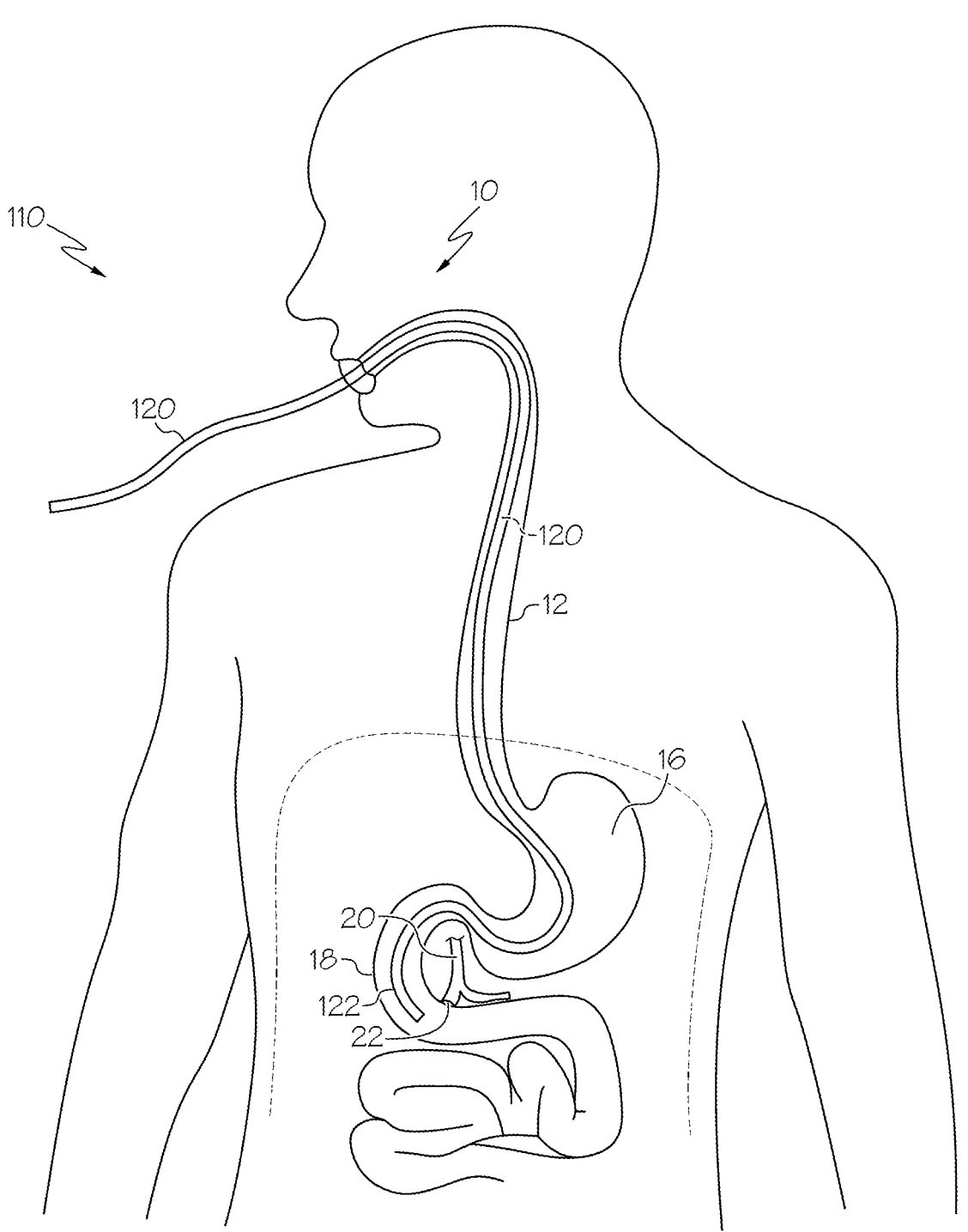
FIG. 4 is a schematic view of the medical instrument of FIG. 1 positioned at a target site of a patient, according to aspects of this disclosure.

Referring now to FIG. 4, an exemplary method of using medical system 100 to extract a target object from within a subject 10 (e.g., patient) is schematically depicted. For example, shaft 120 of medical instrument 100 may be guided through a digestive tract of subject 10 by inserting distal end 122 into a nose or mouth (or other suitable natural body orifice) of the subject's body 10. In embodiments, medical instrument 110 may be inserted through a gastrointestinal tract of the subject's body 10, including an esophagus 12, a stomach 16, and/or into an intestinal tract 18 (including small and large intestines) until reaching a target treatment site, such as a site proximate a common bile duct 20. It should be appreciated that a length of shaft 120 may be sufficient so that a proximal end of medical instrument 110 (including handle 112) is external of the subject's body 10 while distal end 122 of shaft 120 is internal to the subject's body 10.

In some embodiments, the target treatment site within the subject's body 10 may be located within the intestinal tract 18. For example, the target treatment site may include aspects of the pancreatic-biliary system, such as the duodenum of the small intestine. In such examples, the target treatment site may be the ampulla/papilla of Vater 22 located in a portion of the duodenum of the small intestine. It should be understood that the ampulla/papilla of Vater 22 generally forms an opening where the pancreatic duct and the common bile duct 20 empty into the duodenum of the small intestine, with the hepatic ducts and the gall bladder emptying into the common bile duct 20. It should be appreciated that medical system 100 may be used in various suitable procedures, including, for example, endoscopic papillary balloon dilation (EPBD) to remove a target object located within the common bile duct 20, such as a stone (e.g., a gallstone, a biliary stone, etc.). While this disclosure relates to the use of medical system 100 in a digestive tract of the subject's body 10, it should be understood that the features of this disclosure could be used in various other locations (e.g., other organs, tissue, etc.) within the subject's body 10, and to remove various other material from the body 10.

Still referring to FIG. 4, shaft 120 may extend into the subject's body 10 until it reaches a position in which distal end 122 is located proximate to the ampulla/papilla of Vater

22. It should be understood that medical device 130 may be received within medical instrument 100, such as, for example, within shaft 120 (e.g., via port 116) prior to and/or after insertion of medical instrument 110 into the subject's body 10. With distal end 122 positioned at the ampulla/papilla of Vater 22 and medical device 130 disposed within shaft 120, medical device 130 may be actuated via the one or more actuators 136, 138 (see FIG. 1) to move one or more components of extraction assembly 160 distally from the opening at distal end 122.

Accordingly, outer tube 132 may be positioned at the ampulla/papilla of Vater 22 by extending distal end 134 outwardly from the opening at distal end 122. Outer tube 132 may move relative to shaft 120 in response to actuating first actuator 136. In the example, an instrument (e.g., a guidewire) may be received within first lumen 171A of inner tube 170 (see FIG. 2) and extended through the distal opening of inner tube 170. With distal end 134 positioned adjacent to the ampulla/papilla of Vater 22, the guidewire may be received in the common bile duct 20.

Figure 5A:
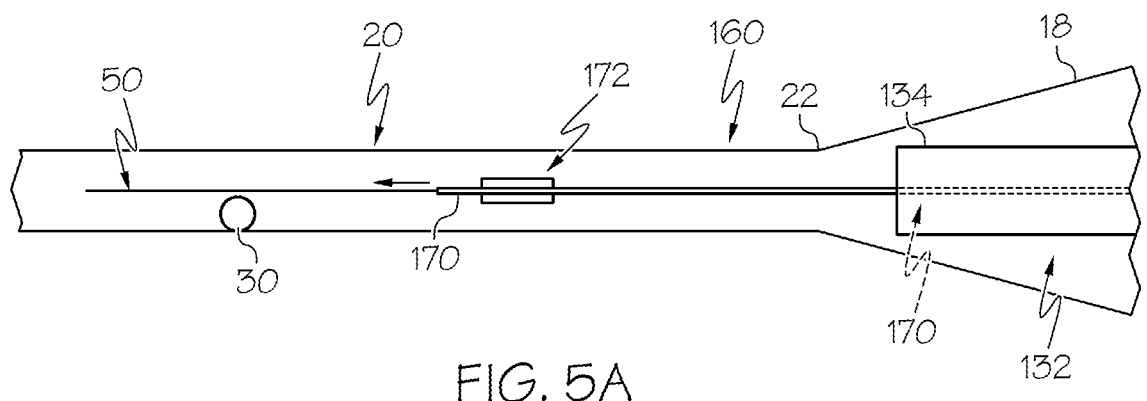
FIG. 5A is a partial side view of the medical instrument of FIG. 1 with a second expandable member of the extraction assembly positioned at the target site and in the deflated state, according to aspects of this disclosure.

Referring now to FIG. 5A, inner tube 170 may be moved relative to outer tube 132 by actuating second actuator 138. In the example, inner tube 170 may translate over the guidewire 50 to guide second expandable member 172 into the common bile duct 20. Second expandable member 172 may be maintained in the deflated state as inner tube 170 moves through the ampulla/papilla of Vater 22 and into the common bile duct 20. Inner tube 170 may be translated through the common bile duct 20 to position second expandable member 172 distally of the target object 30.

Figure 5B:
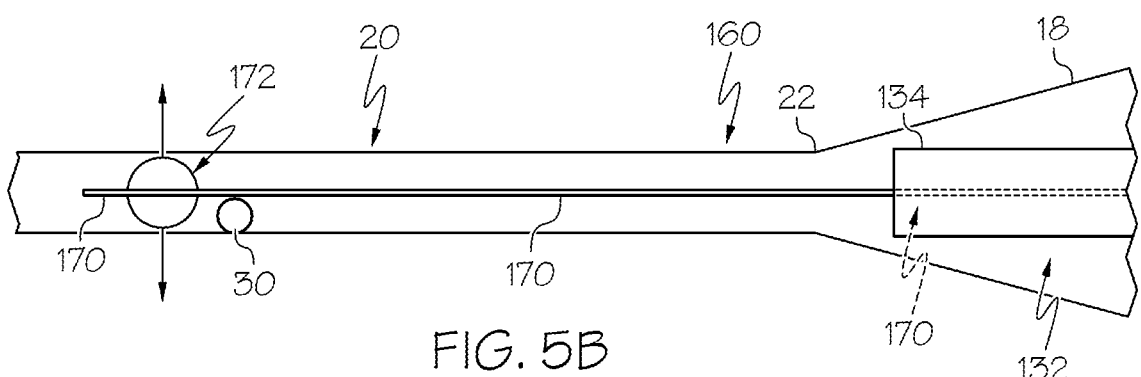
FIG. 5B is a partial side view of the medical instrument of FIG. 1 with the second expandable member of the extraction assembly positioned at the target site and in the inflated state, according to aspects of this disclosure.

Referring to FIG. 5B, with the target object 30 positioned between second expandable member 172 and distal end 134, second expandable member 172 may be transitioned from the deflated state (FIG. 5A) to the inflated state by receiving a pressurized fluid (e.g., gas, liquid) via lumen 171 of inner tube 170 (see FIG. 2). In some embodiments, second expandable member 172 may be configured to abut against adjacent tissue within the common bile duct 20 when transitioned to the inflated state, thereby increasing a lumen size of the common bile duct 20. Expansion of second expandable member 172 may further inhibit movement of the target object 30 relative to the common bile duct 20 and distally past second expandable member 172. It should be appreciated that increasing a diameter of the common bile duct 20 may minimize a force necessary to move the target object 30 toward the ampulla/papilla of Vater 22 and out from the common bile duct 20. Increasing a diameter of the common bile duct 20 with second expandable member 172 may further minimize contact between the target object 30 and the tissue walls of the common bile duct 20. It should be understood that the target object 30 may include one or more sharp edges such that minimizing contact between the target object 30 and the surrounding tissue of the common bile duct 20 may reduce injury to the subject 10.

Figure 5C:
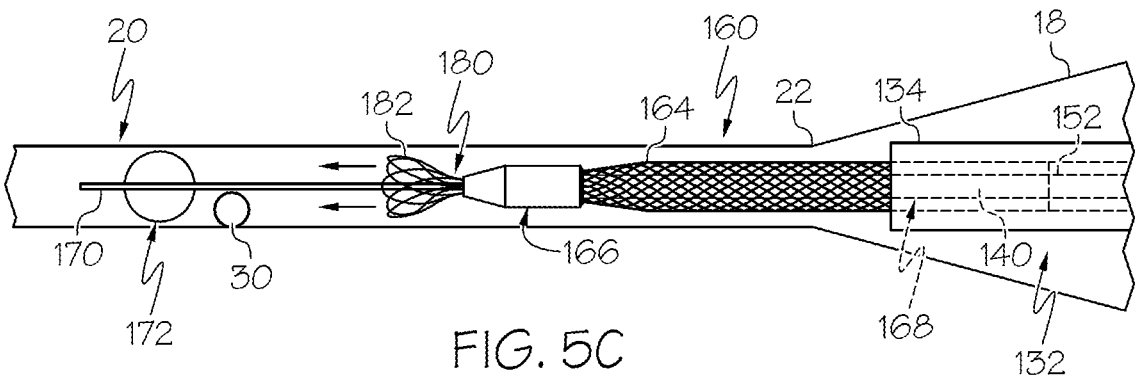
FIG. 5C is a partial side view of the medical instrument of FIG. 1 with the first and third expandable members of the extraction assembly positioned at the target site, in compressed states, and covered by a sheath, according to aspects of this disclosure.

Referring now to FIG. 5C, inner shaft 140 and outer shaft 150 may be moved distally relative to outer tube 132 to extend first expandable member 162 and third expandable member 180 outward from lumen 131 of outer tube 132 (see FIG. 2). For example, inner shaft 140 and outer shaft 150 may be translated in response to actuating first actuator 136 and/or second actuator 138. In other embodiments, outer tube 132 may be moved proximally relative to inner shaft 140 and outer shaft 150 to retract distal end 132 and expose first expandable member 162 and third expandable member 180 from within lumen 131. In the example, body 164 may be maintained in the collapsed state as first expandable member 162 extends outwardly from outer tube 132.

Third expandable member 180 may be transitioned from the collapsed state (see FIG. 3A) to the expanded state as third expandable member 180 moves distally from distal end 134. As described in detail above, the plurality of wires 182 may be configured to move radially outward, relative to inner tube 170, upon removal of a force applied against the plurality of wires 182 by outer tube 132. Inner shaft 140, outer shaft 150, first expandable member 162, and third expandable member 180 may be moved distally through the common bile duct 20 and toward the target object 30 (e.g., by actuating actuators 136, 138) until third expandable member 180 is positioned adjacent to a proximal side of the target object 30. Alternatively, outer tube 132, inner shaft 140, and outer shaft 150 may be moved distally toward the target object 30 to a position proximal to the target object 30. In this instance, medical device 130 may be pulled proximally to expose third expandable member 180, thereby expanding the plurality of wires 182.

Figure 5D:
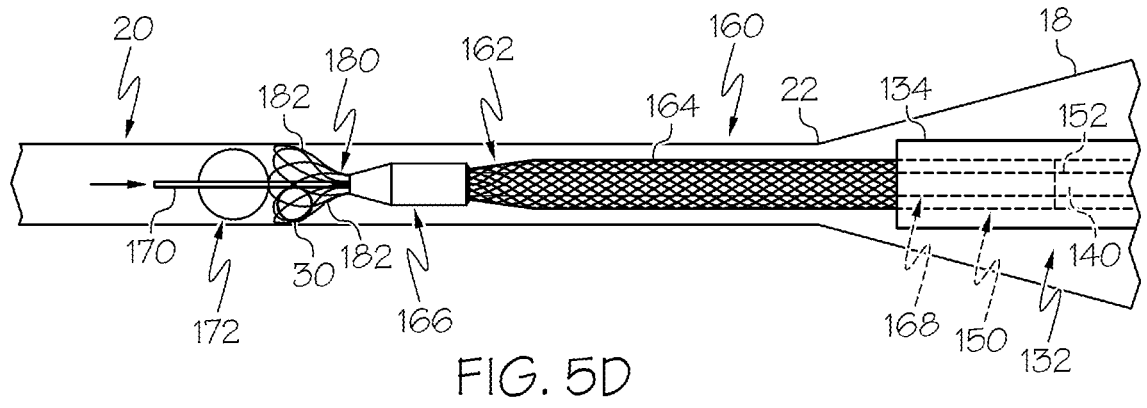
FIG. 5D is a partial side view of the medical instrument of FIG. 1 with the third expandable member receiving a target object located within the target site from the second expandable member, according to aspects of this disclosure.

Referring now to FIG. 5D, with third expandable member 180 in the expanded state and positioned proximal to the target object 30, inner tube 170 may be moved proximally through the common bile duct 20 while inner shaft 140 and outer shaft 150 remain stationary. In this instance, second expandable member 172 may translate toward the third expandable member 180 and abut against a distal side of the target object 30. Second expandable member 172 may be configured to guide the target object 30 through the common bile duct 20 and into the cavity of third expandable member 180 in response to inner tube 170 moving proximally into inner shaft 140 and outer shaft 150.

Third expandable member 180 may be configured to receive the target object 30 within the cavity defined by the plurality of wires 182. In some embodiments, with the plurality of wires 182 flared radially outward when third expandable member 180 is in the expanded state, the plurality of wires 182 may be configured to direct the target object 30 toward a center of the cavity. In this instance, the target object 30 may be completely surrounded by second expandable member 172 and third expandable member 180. Stated differently, extraction assembly 160 may be configured to capture the target object 30 between second expandable member 172 and third expandable member 180 such that movement of the target object 30 is inhibited. For instance, the plurality of wires 182 may be configured to inhibit radial and/or proximal movement of the target object 30 and second expandable member 172 may be configured to inhibit distal movement of the target object 30.

Still referring to FIG. 5D, in some embodiments, the plurality of wires 182 may be configured to move in response to receiving the target object 30 within third expandable member 180. That is, the plurality of wires 182 may change position and/or a configuration relative to one another to accommodate the target object 30 within the cavity. In other embodiments, third expandable member 180 may be omitted entirely such that inner tube 170 may be configured to position the target object 30 between second expandable member 172 and distal end 166 in response to moving proximally into inner shaft 140 and outer shaft 150. In this instance, the target object 30 may engage distal end 166 and be inhibited from moving proximally by body 164.

Figure 5E:
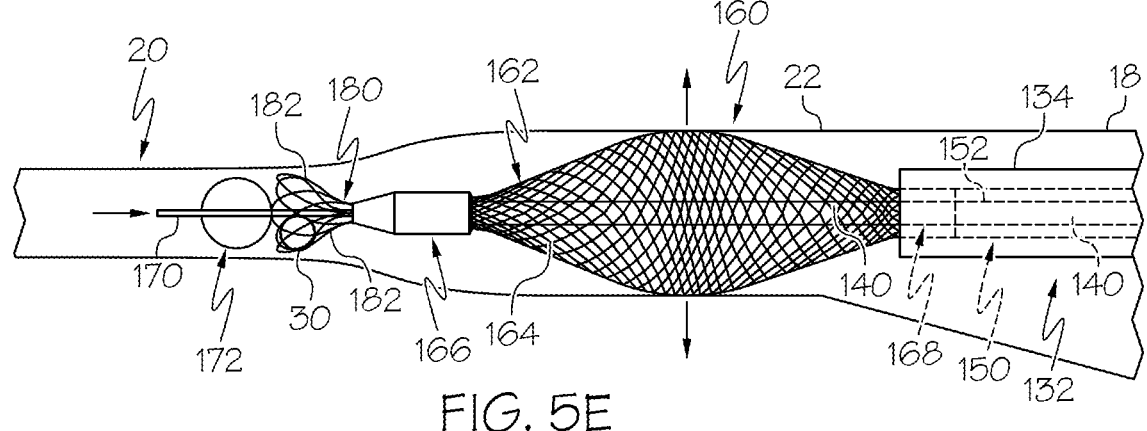
FIG. 5E is a partial side view of the medical instrument of FIG. 1 with the first expandable member of the extraction assembly positioned at the target site and in the expanded state, according to aspects of this disclosure.

Referring to FIG. 5E, first expandable member 162 may be transitioned from the collapsed state to the expanded state in response to actuating one or more of actuators 136, 138. In one example, body 164 may expand radially outward by moving inner shaft 140 proximally relative to outer shaft 150. With distal end 166 secured to inner shaft 140, distal end 166 may be configured to move proximally toward proximal end 168, thereby reducing a longitudinal length of body 164 and increasing a lateral width of body 164. In a further example, body 164 may expand radially outward by moving outer shaft 150 distally relative to inner shaft 140. In this instance, with proximal end 168 secured to outer shaft 150, proximal end 168 may be configured to move distally toward distal end 166, thereby reducing a longitudinal length of body 164 and increasing a lateral width of body 164. In the example, the relative position of inner tube 170, second expandable member 172, and third expandable member 180 may remain the same as these components remain stationary.

A dilation diameter of first expandable member 162 may be incrementally increased by an operator of medical system 100 using the markings on actuators 136, 138. Stated differently, an operator may control an expansion of body 164, and select an appropriate dilation size, by utilizing the markings on actuators 136, 138 to guide dilation of the common bile duct 20 with first expandable member 162. Dilation of the common bile duct 20 and the ampulla/papilla of Vater 22 may be determined based on a size of the target object 30. During dilation of first expandable member 162, body 164 may abut against the surrounding tissue walls of the common bile duct 20, thereby increasing a lumen size of the common bile duct 20 at the ampulla/papilla of Vater 22. In other embodiments, first expandable member 162 may be expanded prior to translating second expandable member 172 proximally toward third expandable member 180. In this instance, increasing a lumen size of the common bile duct 20 prior to pulling the target object 30 into the cavity of third expandable member 180 may facilitate the proximal movement of second expandable member 172.

Figure 5F:
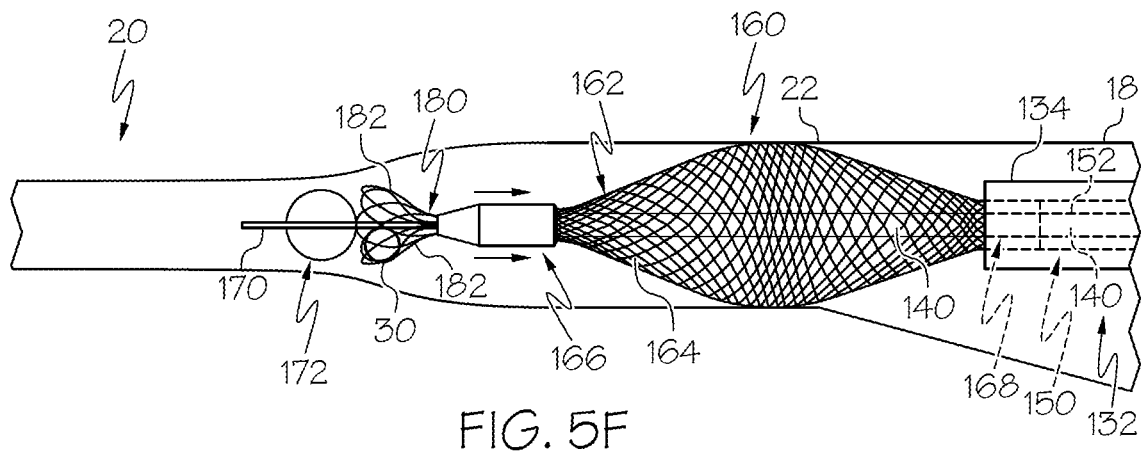
FIG. 5F is a partial side view of the medical instrument of FIG. 1 extracting the target object from the target site, according to aspects of this disclosure.

As seen in FIG. 5F, extraction assembly 160 may be retracted from the common bile duct 20 by moving inner shaft 140, outer shaft 150, and inner tube 170 proximally through the ampulla/papilla of Vater 22 to pull first expandable member 162, second expandable member 172, and third expandable member 180 therethrough. With the target object 30 captured between second expandable member 172 and third expandable member 180, the target object 30 may be extracted from the common bile duct 20. A proximal extraction (e.g., pulling) force necessary to remove the target object 30 may be effectively reduced by first expandable member 162 and second expandable member 172 collectively increasing a diameter of the common bile duct 20 at points proximal to and distal of the target object 30, respectively. In this instance, contact between the target object 30 and the surrounding tissue of the common bile duct 20 may be minimized.

Upon retracting extraction assembly 160 and the target object 30 proximally of the ampulla/papilla of Vater 22, first expandable member 162 may be transitioned to the compressed state and second expandable member 172 may be transitioned to the deflated state (see FIG. 3A). Extraction assembly 160 may be moved proximally relative to outer tube 132 to pull first expandable member 162, second expandable member 172, and third expandable member 180 into lumen 131 (see FIG. 2). With the target object 30 received within third expandable member 180, the target object 30 may be pulled into outer tube 132. In this instance, distal end 134 may move proximally relative to distal end 122 and through shaft 120 to remove medical device 130 from the subject's body 10.

Alternatively, for large target objects 30 (e.g., larger than the working channel of medical instrument 110 and/or the inner diameter of outer shaft 150), outer tube 132 may cover first expandable member 162 and be positioned proximal to third expandable member 180 (e.g., while in the expanded state). In this instance, with second expandable member 172 in the inflated state, medical instrument 110 may be retracted proximally to move outer tube 132 out of the body 10.

Each of the aforementioned systems, devices, assemblies, and methods may be used to extract an object (e.g., a stone) from a target treatment site in a subject (e.g., a patient). By providing a medical device including an extraction assembly having a plurality of expandable members, a user may selectively move and actuate (e.g., expand) the plurality of expandable members relative to one another to capture and extract the stone during a procedure. The plurality of expandable member may receive the stone and increase a size and/or shape of the target treatment site to facilitate removal of the stone therefrom. In this instance, a user may reduce overall procedure time, increase efficiency of procedures, and/or avoid unnecessary harm to a subject's body caused by the use of multiple medical instruments at the target treatment site to perform removal of the object.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:

a first shaft;

a second shaft disposed within and configured to move relative to the first shaft;

a third shaft disposed within and configured to move relative to the second shaft;

a first expandable member having a proximal end secured to the first shaft and a distal end including a tube, wherein the tube is secured to the second shaft; wherein the distal end of the first expandable member is configured to move relative to the proximal end of the first expandable member in response to the second shaft moving relative to the first shaft; and wherein the first shaft and the second shaft are configured to increase a width and decrease a length of the first expandable member when the distal end moves toward the proximal end, and to decrease the width and increase the length of the first expandable member when the distal end moves away from the proximal end;

a second expandable member disposed about the third shaft such that the third shaft extends through the second expandable member, wherein the second expandable member is in fluid communication with a lumen of the third shaft and configured to expand radially outward in response to receiving a fluid from the lumen; and a third expandable member, wherein a proximal end of the third expandable member is received within and secured to a tapered distalmost end of the tube, thereby securing the third expandable member to the second shaft, wherein the third expandable member defines a cavity having a distally-facing opening configured to receive an object, and wherein the third expandable member is configured to engage the object received within the cavity in response to the third shaft moving proximally relative to the second shaft.

2. A medical device, comprising:

an outer shaft;

an inner shaft disposed within the outer shaft;

a tube disposed within the inner shaft and the outer shaft;

a first expandable member having a proximal end secured to the outer shaft and a distal end secured to the inner shaft, wherein the inner shaft and the tube are received through the first expandable member, wherein the distal end of the first expandable member includes a sheath, wherein the sheath secures the distal end of the first expandable member to the inner shaft;

a second expandable member disposed about the tube such that the tube extends through the second expandable member, wherein a distalmost end of the tube extends distally of a distalmost end of the second expandable member, and wherein the tube includes a first lumen that extends to a distal opening at the distalmost end of the tube and a second lumen that terminates proximally of the distalmost end of the tube and is configured to deliver a fluid to the second expandable member; and a third expandable member secured to the inner shaft and positioned distally to the distal end of the first expandable member, and wherein a proximal end of the third expandable member is received within and secured to a distal end of the sheath having an outer surface that has a distally tapered profile, thereby securing the third expandable member to the inner shaft.

3. The medical device of claim 2, wherein the proximal end of the third expandable member is secured to the sheath via crimping.

4. The medical device of claim 3, wherein the third expandable member includes a plurality of wires defining a cavity configured to engage an object received therein, and wherein the plurality of wires have proximal ends that are secured to the sheath via crimping and distal ends that flare radially outward relative to the sheath to define the cavity.

5. The medical device of claim 2, wherein the third expandable member is configured to move from a compressed state to an expanded state, and wherein a distal end of the third expandable member expands radially outward when transitioning from the compressed state to the expanded state.

6. The medical device of claim 2, wherein the distal end of the third expandable member is configured to move radially relative to the proximal end of the third expandable member.

7. The medical device of claim 2, wherein the third expandable member includes a plurality of wires defining a cavity configured to engage an object received therein, and wherein the plurality of wires have distal ends that flare radially outward relative to the distal end of the sheath to define the cavity, such that the cavity is positioned distal to the sheath.

8. The medical device of claim 7, wherein the plurality of wires have proximal ends that are secured to the distal end of the sheath.

9. The medical device of claim 7, wherein the sheath defines an inner surface that is positioned opposite the outer surface having the distally tapered profile, and wherein the plurality of wires have proximal ends that are secured to the inner surface of the sheath.

* * * * *